(12) United States Patent
Witt

(10) Patent No.: US 7,118,660 B2
(45) Date of Patent: Oct. 10, 2006

(54) METHOD AND APPARATUS FOR ANALYZING A MIXTURE OF SAMPLE SUBSTANCES

(75) Inventor: Klaus Witt, Keltern (DE)

(73) Assignee: Agilent Technologies, Inc., Palo Alto, CA (US)

( * ) Notice: Subject to any disclaimer, the term of this patent is extended or adjusted under 35 U.S.C. 154(b) by 471 days.

(21) Appl. No.: 10/400,351

(22) Filed: Mar. 27, 2003

(65) Prior Publication Data

US 2004/0031684 A1 Feb. 19, 2004

(30) Foreign Application Priority Data

Aug. 16, 2002 (EP) .................... 02018522

(51) Int. Cl.
*G01N 27/447* (2006.01)
*G01N 27/453* (2006.01)
(52) U.S. Cl. ............... 204/452; 204/451; 204/603; 204/601; 422/70
(58) Field of Classification Search ........ 204/451–455, 204/601–605; 422/70
See application file for complete search history.

(56) References Cited

U.S. PATENT DOCUMENTS 5,131,998 A * 7/1992 Jorgenson et al. ............ 210/93
5,167,790 A 12/1992 Carle et al. ............. 204/299 R
6,387,234 B1 * 5/2002 Yeung et al. ................ 204/451
2002/0025576 A1 2/2002 Northrup et al. ........ 435/288.5
2002/0098595 A1 7/2002 Lubman et al. ............. 436/178

FOREIGN PATENT DOCUMENTS

WO WO 0708331 A1 * 4/1995
WO WO 01/71330 9/2001
WO WO 02/13122 2/2002

OTHER PUBLICATIONS

Savage, J., Examiner. European Search Report EP 02 01 8522 dated Jan. 28, 2003.
Poole, Colin F. "Planar chromatography at the turn of the century," Journal of Chromatography, vol. 856, No. 1-2, Sep. 24, 1999, pp. 399-427, XP 004180088.

* cited by examiner

*Primary Examiner*—Alex Noguerola

(57) ABSTRACT

An apparatus for analyzing a mixture of sample substances comprises a fluid-guiding structure wherein the sample substances are moving essentially in one dimension along the structure and are subject to at least two separation mechanisms, such as capillary electrochromatography (CEC) and capillary zone electrophoresis using high voltage. The signals from a detection means are supplied to a signal processing means, which derives a parameter therefrom which in turn is used to derive improved measuring results for each of the separation results associated with the various separation mechanisms, respectively. The apparatus can be used for protein analysis, for example in combination with a mass spectrometer.

8 Claims, 2 Drawing Sheets

METHOD AND APPARATUS FOR ANALYZING A MIXTURE OF SAMPLE SUBSTANCES

The invention relates to a method and a corresponding apparatus for analyzing a mixture of sample substances. Such a method can be used for identifying chemical or biochemical substances in a mixture and for determining the concentration of these substances. The method can be used, for example, for analyzing proteins.

BACKGROUND OF THE INVENTION

The field of analytical chemistry and biochemistry is concerned with the measurement of composition, amounts and properties of substances, such as solutions of chemicals, biochemical substances, or other analytes. An important biochemical project that has been completed in the past years is the human genome project. This project has brought up a new business field, pharmacogenomics, which has the goal to understand biological functions and to influence such functions by specific interventions with pharmaceutical substances. By comparing protein-expression after drug treatment with protein expression in untreated condition, it is possible to relate the observed changes to the effects or function of the drug. Recent works have shown that there is a lack of correlation between transcriptional profiles and actual protein levels in cells. Protein analysis has therefore become indispensable and complementary to genomic analysis in order to obtain an accurate picture of cellular function and metabolism.

Methods and apparatus have been developed to enable detection or identification of analytes in smaller and smaller amounts or under more useful conditions. In particular, protein analysis requires speedy execution and high separation efficiency if applied as a screening method for various cell and tissue types. The established method for protein expression monitoring is gel electrophoresis on polyacrylamide (PAGE). While this is efficient as a preparative method, it is by far too slow for screening applications. It requires a lot of time involvement of an operator, and often the separated spots have to be cut out manually from these preparations so that they can subsequently be analyzed in a Maldi-TOF-MS system (Maldi: matrix assisted laser desorption ionization; TOF:time-of-flight; MS: mass spectrometry).

Often it is difficult to achieve enough separation or peak capacity in order to detect and identify all individual fragments of a sample in just one run. This limitation usually is a reason to use two-dimensional separation devices wherein a hybrid of two separation mechanisms is formed. Examples for such two-dimensional separations are: ion exchange/reversed phase liquid chromatography, or isoelectric focusing (IEF)/SDS-PAGE, which is called two-dimensional gel electrophoresis (2D-GE). Regarding state of the art, it is referred to the article, G. L. Corthals et al.: "The dynamic range of protein expression: A challenge for proteomic research", Electrophoresis 2000, 21/6, pages 1104–1115; and V. C. Wasinger et al.: "Proteomic tools for biomedicine", Journal of Chromatography B, 771 (2002), pages 33–48.

In the pharmaceutical industry, high throughput screening is often required. In order to screen for statistically relevant parameters, a large number of analysis steps are performed in parallel. High throughput screening requires automation, speed and reliable operation. In this approach often all the 2D-GE platforms cannot fulfill the requirements.

Several attempts have been made to create an automated two-dimensional separation arrangement. In one approach, liquid chromatography is combined with capillary electrophoresis. In another approach, disclosed in EP-A 977030, a two-dimensional electrophoresis separation device is implemented on a microchip.

The mentioned devices and methods have their primary applications in the field of proteomics. There is such a broad variety of proteins that a simple uni-dimensional separation quickly reaches its limits. Furthermore, the interesting proteins in a sample indicating specific disorders or diseases often are only present in small quantities, whereas there is a substantially larger portion of proteins in the sample which are not of particular interest. This has the consequence that small, but interesting peaks in the measuring results are concealed under tall peaks which are of no particular interest for the actual analysis, which in turn requires even more peak capacity to get clearer, more distinct readings.

Reliable results in the field of proteomics are so important that one even has to take the trouble of several-days measurements in order to produce a clear distinct two-dimensional pattern. It has been common to run a two-dimensional gel electrophoresis, cut out the corresponding spots to extract a clean population and then to run it on a Maldi-MS or even a sequencer, see also Mary F. Lopez: "Better approaches to finding the needle in a haystack: Optimizing proteome analysis through automation", Electrophoresis, Vol. 21, Issue 6 (2000), Pages 1082–1093.

SUMMARY OF THE INVENTION

It is thus an object of the invention to provide a method and a corresponding apparatus for analyzing a mixture of sample substances, which allows to achieve similar or better separation results as the two-dimensional methods of the prior art, and which is easily automated and which is more suitable for high-throughput operation.

It is also an object of the invention to provide a method and an apparatus for fast and accurate protein analysis with high resolution.

According to the invention, these objects are achieved by a method as defined in claim 1 and by an apparatus as defined in claim 10. The method according to the invention is thus defined by a process wherein the sample substances are moving essentially in one dimension defined by a fluid-guiding structure, such as a capillary or a channel, wherein the sample substances are subject to at least a first separation mechanism and a second separation mechanism within said fluid-guiding structure, wherein the sample substances are detected for providing detection signals, and wherein at least one parameter is derived from said detection signals, which is used for deriving at least first separation results associated with the first separation mechanism and second separation results associated with the second separation mechanism.

It is an underlying idea of the invention to combine several separation modes in a way that the final physical separation actually does not have to be perfect, but that with sophisticated detection of multiple parameters additional information can be derived allowing the calculation of clean bands of sample substances. In that way, a reliable identification of the sample substances is possible, even if the sample substances have not been separated completely at the locations where they have been detected.

The invention has the additional advantage that all sample components are moving towards a single physical outlet, which is ideal for interfacing a mass spectrometer or a NMR apparatus. In the two-dimensional arrangements of the prior art the sample substances are spread over several axes, which requires a full-area detection, whereas the invention permits to record the concentration at a specific location. In case of a mass spectrometer coupled to an apparatus of the invention, this location may be the atmospheric pressure ionization source (API source).

In an embodiment of the invention a timing or speed measurement is used to derive additional information. Either the time difference between occurrences at different detection locations is derived, or a more complex approach with Fourier detection may be used. Also, a photodiode array arranged along the fluid-guiding structure may be used to monitor movement of the bands. A photodiode array as such is known, in a different connection, from EP-A 840113, with the title "Microchip Electrophoretic Method and Apparatus". Based on the geometric design of the set-up the path of movement of the sample is known. From the actual speed and total time it is possible to calculate the specific parameters for each dimension.

The concept of the invention can also be realized for 3 or more dimensions. Also, the orthogonal measurement parameter does not necessarily have to be speed or timing. Other parameters can be selected from, but are not limited to, charge state, conductivity, viscosity, temperature, pH, dipole moment, or affinity, if these parameters are indicative of a significant factor in the separation in either of the anticipated dimensions.

The invention thus provides a mechanically simple apparatus which operates in one dimension, but which allows to derive separation information, which would otherwise only be accessible by a two-dimensional separation.

BRIEF DESCRIPTION OF THE DRAWINGS

In the following embodiments of the invention will be explained with reference to the drawings.

DETAILED DESCRIPTION

Figure 1:
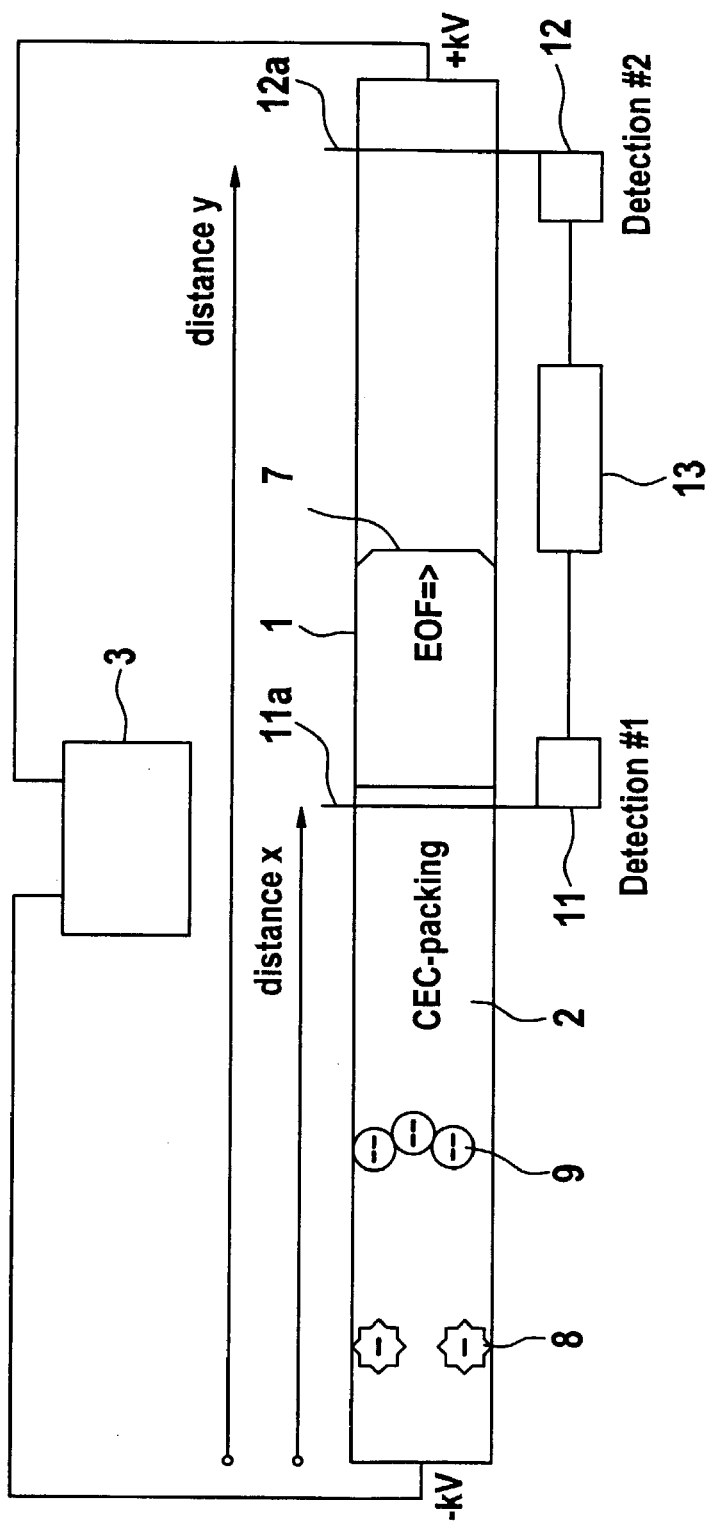
FIG. 1 is a schematic diagram of a first embodiment of the invention.

In the embodiment of the invention shown in FIG. 1, a capillary 1 is packed with packing material 2, and the ends of the capillary are connected to a high voltage power supply 3, respectively. The packing material 2, which fills the left portion of the capillary 1, is of the type, which is used, in capillary electrochromtography (CEC). Sample substances, such as proteins, which have been introduced into the capillary, are moved through the capillary by means of the electric field provided by the power supply 3. The movement due to the electric field is dependent on the mobility of the sample substances, respectively. Since there is an interaction between the sample substances and the packing material 2, there is also retention in the capillary which is dependent on the specific sample substance. Thus, there are combined separation modes in the capillary, i.e., retention and electromigration.

A first detector 11 is arranged near the end of the packing 2 and a second detector 12 is arranged near the end of the capillary 1. The detectors may be of any type, for example absorbance detectors may be used for protein analysis, fluorescence detectors may be used for DNA analysis. Other detectors, such as conductivity detectors, may also be used for specific applications. In the embodiment shown, the two detectors are of the same type, but it is also possible to use detectors of different types.

In FIG. 1, the detectors are only shown schematically. The lines 11a and 12a designate the locations in the capillary where sample substances are detected. The output signals of the detectors 11 and 12 are supplied to a data processing unit 13, which derives more refined measuring results from the two input signals in a way which will be described below.

Figure 2:
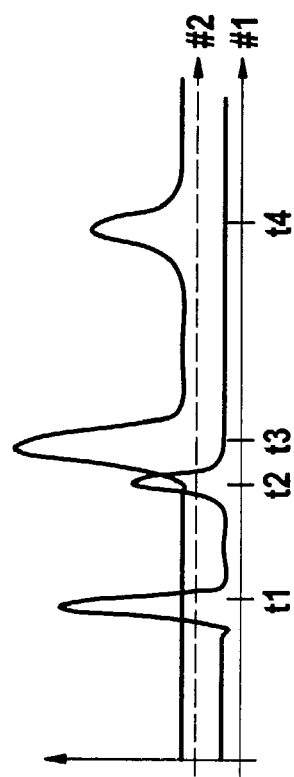
FIG. 2 shows the detector output signals as a function of time in the embodiment of FIG. 1.

FIG. 1 shows as an example two-separated sample substances 8 and 9. These two sample substances pass the first detector 11 at different times t1 and t2 respectively. This is illustrated in FIG. 2, wherein the detector output signal of detector 11 as a function of time is shown as curve #1, and the detector output signal of detector 12 is shown as curve #2. The area of the peaks is a measure of the sample concentration. After the substances 8 and 9 have been detected by the detector 11 they are moving to the detector 12 under the influence of the electric field in the capillary, without retention taking place. The substances 8 and 9 are then measured by the detector 12 at times t3 and t4, respectively. From the time differences t3–t1 and t4–t2 the mobilities of the substances 8 and 9, respectively, are determined by the data processing unit 13, based on the known electric field strength in the capillary and on the known distance between the two detectors.

Figure 3:
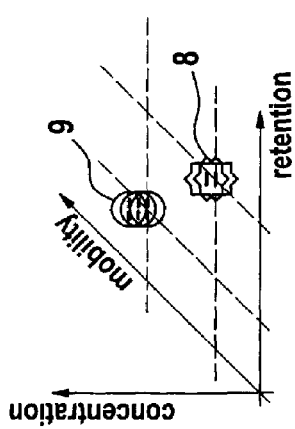
FIG. 3 is a graphical representation of concentration vs. mobility and retention factor as derived in the embodiment of FIG. 1.

From the determined mobility values of the sample substances 8,9 and from the measurements by detector 11, the retention factors of the sample substances can be determined. The final result is shown in FIG. 3, which is a graphical representation of mobilities and retention factors for the various sample substances and of the corresponding concentrations. On the basis of the determined retention factor and mobility of a specific sample substance, a precise identification of this sample substance is possible, for example by using data bases of known mobilities and retention factors.

In capillary electrophoresis, there is typically a phenomenon called electroosmotic flow (EOF) which is more or less pronounced depending on factors such as the material of the inner capillary wall etc. If EOF occurs in an apparatus of the invention (FIG. 1, reference numeral 7), it does not contribute to the separation of sample substances, but it still has an influence on the times when peaks arrive at the point of detection. The EOF, however, can be measured and taken into account when determining the mobilities of the sample substances, for example by providing known marker substances in the liquid transported through the capillary, see, for example U.S. Pat. No. 5,316,630, with the title "Methods for Chromatography Analysis". In an embodiment of the invention, one may also use an off-line approach of the type described in U.S. Pat. No. 5,009,760, with the title "Measuring Electrokinetic Properties", or an on-line approach of the type described in U.S. Pat. No. 4,456,513, with the title "Measuring Electrophoretic Mobility" or in U.S. Pat. No. 5,441,613, with the title "Realtime Monitoring, Measurement and Control of EOF".

Figure 4:
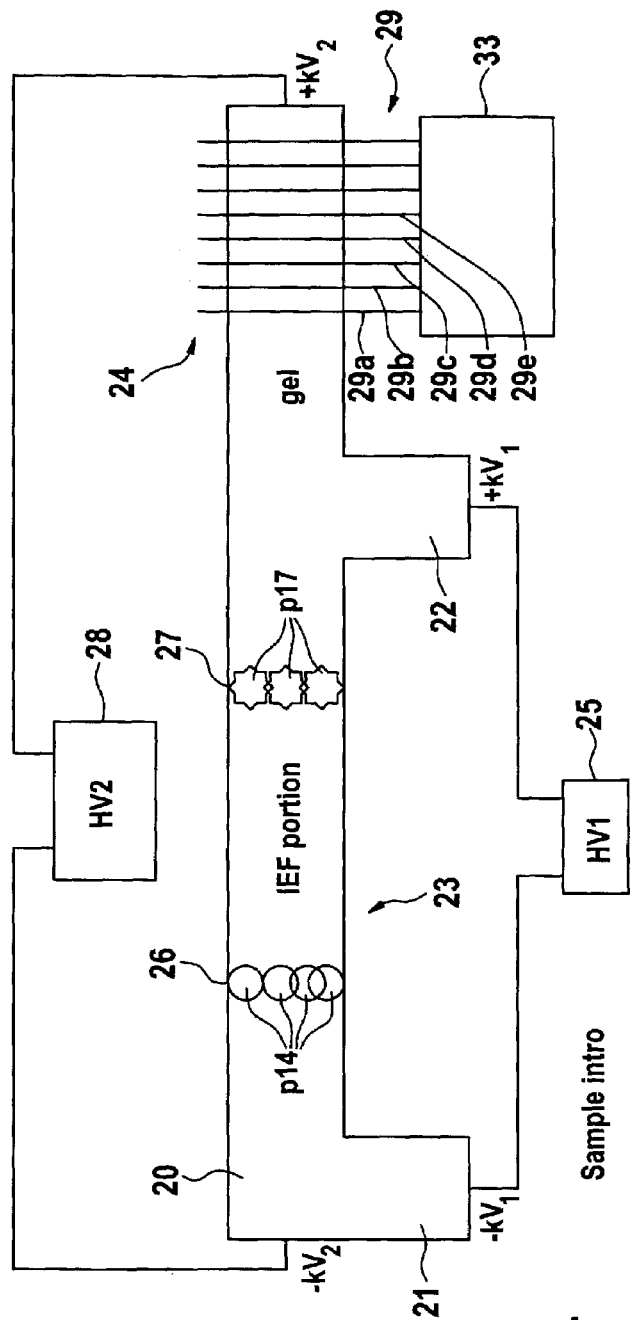
FIG. 4 is a schematic diagram of a second embodiment of the invention.

A second, more complex embodiment of the invention is shown in FIG. 4. This embodiment is implemented in lab-on-a-chip technology wherein small channels through which liquids can be transported are arranged on a microfluidic chip. The chip can be made, for example, of glass or plastic material. FIG. 4 shows a main channel 20 and two side channels 21,22 on a microfluidic chip. The arrangement is designed to have two portions, namely a portion 23 for performing isoelectric focusing (IEF), and a gel-filled sizing portion 24.

With the help of a high voltage supply 25 sample substances are introduced into the main channel 20 through the side channel 21 and then focused. Different sample substances in the channel are illustrated with reference numerals 26 and 27. After sample introduction and focusing a high voltage is applied along the channel 20 with a second high voltage supply 28. This high voltage mobilizes the bands towards the portion 24, where the gel effects additional separation according to the size of the sample substances.

A detection arrangement 29 is used to monitor the absorbance inside the gel to derive information about concentration and speed of movement of the sample substances. The detection arrangement comprises two or more detection spots 29a, 29b, 29c, etc. The detection arrangement may, for example, be of the type described in U.S. Pat. No. 5,699,157, wherein a channel is irradiated through an optical mask while the substances are moving through the channel and wherein the light detected with a photodetector is analyzed, e.g. by Fourier analysis. Alternatively, several light sources and several photodetectors arranged opposite to the light sources, respectively, could be used to determine concentration and velocity of the sample substances. Such an arrangement is disclosed, in a different connection, in U.S. Pat. No. 5,303,021, with the title "Optical Detection for Capillary Chromatography". The output signals from the detection arrangement 29 in FIG. 1 are supplied to a signal processing unit 33 wherein they are further processed to derive improved separation information.

Two bands that have been separated in the IEF portion 23 may still arrive at the detector at the same time. But with the knowledge of the speed at the point of detection it is possible to calculate at which positions these bands started, respectively, i.e. the specific positions in the original pH gradient. Measuring speed generally can provide information about the size of sample substances, but measuring speeds at specific points in time allows to derive information about the pI (isoelectric point). The pH of a solution in which a particular amino acid does not migrate under the influence of an electric field is called the isoelectric point of that particular amino acid. At its pI a protein loses its net charge due to a pH-induced change in dissociation stage.

It is understood that other detection arrangements than those described in connection with FIGS. 1 and 4 can be used. For example, one could use an arrangement of photodiodes, such as a photodiode array, along the separation capillary to monitor the movement of sample substances.

The invention claimed is:

1. A method of analyzing a mixture of sample substances, wherein the sample substances are moving essentially in one dimension defined by a fluid-guiding structure, such as a capillary or a channel,
wherein the sample substances are subject to at least a first separation mechanism and a second separation mechanism, wherein said first and second separation mechanisms are within said fluid-guiding structure, wherein the sample substances are detected for detection signals, wherein said detection signals are provided at least at two different detection locations along the fluid-guiding structure, wherein the detection signals are received by first and second detectors, wherein timing information about the points in time of the occurrences of the sample substances at said at least two detection locations is derived, wherein said timing information is used to derive at least one parameter, and wherein said at least one parameter is used for deriving at least first separation results associated with the first separation mechanism and second separation results associated with the second separation mechanism.

2. Method as in claim 1, wherein the first separation mechanism is capillary electrochromatography and the second separation mechanism is capillary zone electrophoresis.

3. Method as in claim 1, wherein the timing information is used to derive the electrophoretic mobility of the sample substances, and wherein the electrophoretic mobility of the sample substances is used to derive improved retention factors for the sample substances subject to the first separation mechanism.

4. An apparatus for analyzing a mixture of sample substances, comprising:
a fluid-guiding structure, such as a capillary or channel or a network of channels, wherein the sample substances move essentially in one dimension along the fluid-guiding structure;
a first separation mechanism in the fluid-guiding structure;
a second separation mechanism in the fluid-guiding structure;
a detection means arranged along the fluid-guiding structure, wherein the detection means comprises a first and a second detector, wherein said first and second detectors are adapted to receive detection signals; and
a signal processing means coupled to the detection means, wherein the signal processing means and the first and second detectors are operative to derive timing information about the sample substances at the first and second detectors, wherein the timing information is used for deriving at least one parameter, and wherein the at least one parameter is used for deriving at least first separation results associated with the first separation mechanism and second separation results associated with the second separation mechanism.

5. Apparatus as in claim 4 wherein the first separation mechanism comprises a capillary electrochromatography packing and a high voltage means to generate an electric field in the fluid-guiding structure.

6. Apparatus as in claim 4, wherein the detection means comprises an absorbance detector.

7. Apparatus as in claim 4, wherein the detection means comprises an array of photodetectors.

8. Apparatus as in claim 4, wherein the fluid-guiding structure is arranged on a microfluidic chip.

* * * * *